US006645995B2

(12) United States Patent
Kanstrup et al.

(10) Patent No.: US 6,645,995 B2
(45) Date of Patent: Nov. 11, 2003

(54) THERAPEUTICALLY ACTIVE AND SELECTIVE HETEROCYCLIC COMPOUNDS THAT ARE INHIBITORS OF THE ENZYME DPP-IV

(75) Inventors: Anders Kanstrup, Espergaerde (DK); Jane Marie Lundbeck, Glostrup (DK); Lise Brown Christiansen, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/076,577

(22) Filed: Feb. 8, 2002

(65) Prior Publication Data

US 2002/0103384 A1 Aug. 1, 2002

Related U.S. Application Data

(62) Division of application No. 09/767,354, filed on Jan. 23, 2001, now Pat. No. 6,380,398.
(60) Provisional application No. 60/178,856, filed on Jan. 28, 2000, and provisional application No. 60/216,202, filed on Jul. 6, 2000.

(30) Foreign Application Priority Data

Jan. 24, 2000 (DK) .......................................... 2000 00112
Jun. 23, 2000 (DK) .......................................... 2000 00983

(51) Int. Cl.$^7$ .................. A61K 31/4025; C07D 207/18
(52) U.S. Cl. ...................... 514/422; 548/518; 548/530; 548/540; 514/423
(58) Field of Search ................................ 548/518, 530, 548/540; 514/422

(56) References Cited

U.S. PATENT DOCUMENTS

| 6,011,155 A | 1/2000 | Villhauer | .................... 544/333 |
| 6,110,949 A | 8/2000 | Villhauer | .................... 544/333 |
| 6,124,305 A | 9/2000 | Villhauer | .................... 514/272 |

FOREIGN PATENT DOCUMENTS

| DE | 196 16 486 A1 | 10/1997 |
| DE | 198 34 591 A1 | 2/2000 |
| WO | WO 98/19998 | 5/1998 |
| WO | WO 99/38501 | 8/1999 |
| WO | WO 00/34241 | 6/2000 |

*Primary Examiner*—Joseph K. McKane
*Assistant Examiner*—Golam M M Shameem
(74) *Attorney, Agent, or Firm*—Rosemarie R. Wilk-Orescan; Reza Green

(57) ABSTRACT

Described are compounds of formula I

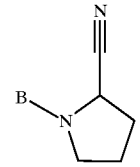

Formula I wherein at least one of the bonds in the five-membered ring is a double bond; B is any alpha or beta amino acid connected to the ring with an amide or peptide bond; or a salt thereof with a pharmaceutically acceptable acid or base. Pharmaceutical compositions containing these compounds are also described. These compounds are useful for treating type II diabetes.

12 Claims, No Drawings

THERAPEUTICALLY ACTIVE AND SELECTIVE HETEROCYCLIC COMPOUNDS THAT ARE INHIBITORS OF THE ENZYME DPP-IV

CROSS-REFERENCE TO RELATED APPLICATIONS

This application is a divisional of U.S. Ser. No. 09/767,354 now U.S. Pat. No. 6,380,398 filed on Jan. 23, 2001, and claims priority under 35 U.S.C. 119 of Danish application no. PA 2000 00112 filed on Jan. 24, 2000, Danish application no. PA 2000 00983 filed on Jun. 23, 2000, U.S. provisional application No. 60/178,856 filed on Jan. 28, 2000, and U.S. provisional application No. 60/216,202 filed on Jul. 6, 2000, the contents of which are fully incorporated herein by reference.

FIELD OF INVENTION

The present invention relates to new therapeutically active and selective inhibitors of the enzyme DPP-IV, pharmaceutical compositions comprising the compounds and the use of such compounds, and the manufacture of medicaments for treating diseases that are associated with proteins which are subject to inactivation by DPP-IV, such as type II diabetes and obesity.

BACKGROUND OF THE INVENTION

Dipeptidyl peptidase-IV (DPP-IV), a serine protease belonging to the group of post-proline/alanine cleaving amino-dipeptidases, specifically removes the two N-terminal amino acids from proteins having proline or alanine in position 2.

Although the physiological role of DPP-IV has not been completely established, it is believed to play an important role in neuropeptide metabolism, T-cell activation, gastric ulceration, functional dyspepsia, obesity, appetite regulation, impaired fasting glucose (IFG) and diabetes.

DPP-IV has been implicated in the control of glucose metabolism because its substrates include the insulinotropic hormones glucagon like peptide-1 (GLP-1) and gastric inhibitory peptide (GIP). GLP-1 and GIP are active only in their intact forms; removal of their two N-terminal amino acids inactivates them.

In vivo administration of synthetic inhibitors of DPP-IV prevents N-terminal degradation of GLP-1 and GIP, resulting in higher plasma concentrations of these hormones, increased insulin secretion and, therefore, improved glucose tolerance. Therefore, such inhibitors have been proposed for the treatment of patients with type II diabetes, a disease characterized by decreased glucose tolerance.

Unfortunately, the post-proline/alanine cleaving aminodipeptidases are also implicated in the regulation of the immune system and inhibitors of these enzymes reportedly suppress immune responses. Thus, there is a risk that long-term treatment of type II diabetes with inhibitors of these enzymes may, as a side effect, lead to immuno-suppression.

However, with the recent discoveries of other post-proline/alanine cleaving amino-dipeptidases that share the same substrate and inhibitor specificity as DPP-IV, including DPP-IVb, Attractin, X and QPP, it has become clear that such inhibitors may inhibit multiple members of this group of enzymes. The precise physiological role of each of these post-proline/alanine cleaving enzymes is not well defined. Consequently, it is not clear what the physiological effect would be of inhibiting each of them separately, a subset, or all of them at the same time.

Diabetic dyslipidemia is characterized by multiple lipoprotein defects, including moderately high serum levels of cholesterol and triglycerides, small LDL particles, and low levels of HDL cholesterol. The results of recent clinical trials reveal beneficial effects of cholesterol lowering therapy in diabetic and nondiabetic patients, thus supporting increased emphasis on treatment of diabetic dyslipidemia. This need for intensive treatment of diabetic dyslipidemia was advocated by the National Cholesterol Education Program's Adult Treatment Panel II.

Obesity is a well-known risk factor for the development of many very common diseases such as atherosclerosis, hypertension and diabetes. The incidence of obese people and thereby also these diseases is increasing throughout the entire industrialized world. Except for exercise, diet and food restriction no convincing pharmacological treatment for reducing body weight effectively and acceptably currently exist. However, due to its indirect but important effect as a risk factor in mortal and common diseases it will be important to find treatment for obesity or appetite regulation. Even mild obesity increases the risk for premature death, diabetes, hypertension, atherosclerosis, gallbladder disease and certain types of cancer. In the industrialized western world the prevalence of obesity has increased significantly in the past few decades. Because of the high prevalence of obesity and its health consequences, its prevention and treatment should be a high public health priority.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

Thus there remains today a need in the art for compounds that are useful for inhibiting DPP-IV without suppressing the immune system.

Several compounds have been shown to inhibit DPP-IV, but all of these have limitations in relation to the potency, stability, selectivity, toxicity, and/or pharmacodynamic properties.

Such compounds have e.g. been disclosed in WO 98/19998, WO 00/34241, U.S. Pat. No. 6,124,305 (Novartis AG) and WO 99138501 (Trustees of Tufts University).

Thus, there is a need for novel DPP-IV inhibitors that are superior with respect to one or more of the above listed properties, and which will be useful for the treatment of conditions, which may be regulated or normalized by inhibition of DPP-IV.

SUMMARY OF THE INVENTION

The present invention provides novel 2-substituted unsaturated heterocyclic compounds, wherein a nitrogen atom in the heterocyclic ring is attached via an amide bond or a peptide bond to an amino acid or an amino acid derivative. These compounds are potent and selective inhibitors of DPP-IV, and are effective in treating conditions that may be regulated or normalized via inhibition of DPP-IV. The invention also concerns pharmaceutical compositions comprising the compounds, a method of inhibiting DPP-IV comprising administering to a patient in need of such treatment a therapeutically effective amount thereof, the compounds for use as a pharmaceutical, and their use in a process for the preparation of a medicament for treating a condition which may be regulated or normalized via inhibition of DPP-IV.

Definitions

The term "DPP-IV" as used herein is intended to mean Dipeptidyl peptidase IV (EC 3.4.14.5; DPP-IV), also known as CD26. DPP-IV cleaves a dipeptide from the N terminus of a polypeptide chain containing a proline or alanine residue in the penultimate position.

The term "treatment" is defined as the management and care of a patient for the purpose of combating the disease, condition, or disorder and includes the administration of a compound of the present invention to prevent the onset of the symptoms or complications, or alleviating the symptoms or complications, or eliminating the disease, condition, or disorder.

The term "beta cell degeneration" is intended to mean loss of beta cell function, beta cell dysfunction, and death of beta cells, such as necrosis or apoptosis of beta cells.

The term "$C_1$–$C_{10}$ alkyl" as used herein, alone or in combination, refers to a straight or branched, saturated hydrocarbon chain having from 1–10 carbon atoms such as but not limited to e.g. methyl, ethyl, n-propyl, isopropyl, n-butyl, sec. Butyl, isobutyl, tert. Butyl, n-pentyl, 2-methylbutyl, 3-methylbutyl, n-hexyl, 4-methylpentyl, neopentyl, 2,2-dimethylpropyl and the like.

The term "$C_2$–$C_{10}$-alkenyl" used herein, alone or in combination, refers to a straight or branched, unsaturated hydrocarbon chain having from 2–10 carbon atoms and at least one double bond such as, but not limited to, vinyl, 1-propenyl, allyl, isopropenyl, n-butenyl, n-pentenyl and n-hexenyl and the like.

The term "$C_2$–$C_{10}$-alkynyl" as used herein, alone or in combination, refers to an unsaturated hydrocarbon chain having from 2–10 carbon atoms and at least one triple bond such as but not limited to —C≡CH, —C≡CCH$_3$, —CH$_2$C≡CH, —CH$_2$—CH$_2$—C≡CH, —CH(CH$_3$)C≡CH and the like.

The term "$C_{1-10}$-alkoxy" as used herein, alone or in combination is intended to include those $C_{1-10}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy and hexoxy. Examples of branched alkoxy are isoprpoxy, sec-butoxy, tert-butoxy, isopentoxy and isohexoxy. Examples of cyclic alkoxy are cyclopropyloxy, cyclobutyloxy, cyclopentyloxy and cyclohexyloxy.

The term "$C_3$–$C_{10}$ cycloalkyl" as used herein refers to a radical of one or more saturated cyclic hydrocarbon having from 3–10 carbon atoms such as, but not limited to, cyclopropyl, cyclobutyl, cyclopentyl, cyclohexyl, adamantyl and the like.

The term "$C_3$–$C_{10}$ cycloalkane" as used herein refers to a saturated cyclic hydrocarbon having from 3–10 carbon atoms such as, but not limited to, cyclopropane, cyclobutane, cyclopentane, cyclohexane, adamantane and the like.

The term "$C_5$–$C_{10}$ cycloalkenyl" as used herein refers to a radical of one or more cyclic hydrocarbon having at least one double bond having from 5–10 carbon atoms such as, but not limited to, cyclopentenyl, cyclohexenyl and the like.

The term "aryl" as used herein includes carbocyclic aromatic ring systems. Aryl is also intended to include the partially hydrogenated derivatives of the carbocyclic systems.

The term "heteroaryl" as used herein includes heterocyclic unsaturated ring systems containing one or more heteroatoms selected from nitrogen, oxygen and sulphur such as furyl, thienyl, pyrrolyl. Heteroaryl is also intended to include the partially hydrogenated derivatives of the heterocyclic systems enumerated below.

The terms "aryl" and "heteroaryl" as used herein refers to an aryl which can be optionally substituted or a heteroaryl which can be optionally substituted and includes phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo [b]thiophenyl (2-(2,3-dihydro-benzo[b]thiophenyl), 3-(2,3-dihydro-benzo [b]thiophenyl), 4-(2,3-dihydro-benzo[b]thiophenyl), 5-(2,3-dihydro-benzo [b]thiophenyl), 6-(2,3-dihydro-benzo[b]thiophenyl), 7-(2,3-dihydro-benzo [b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl, benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl).

DETAILED DESCRIPTION OF THE INVENTION

The present invention provides compounds of formula I

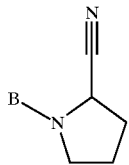

Formula I wherein at least one of the bonds in the five-membered ring is a double bond;

B is any alpha or beta amino acid connected to the ring with an amide or peptide bond;

or a salt thereof with a pharmaceutically acceptable acid or base.

In a preferred embodiment the invention provides compounds of formula II

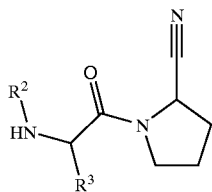

Formula II wherein at least one of the bonds in the five-membered ring is a double bond;

$R^2$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$-alkynyl optionally substituted with one or more $R^4$ independently; $C_3$–$C_{10}$-cycloalkyl optionally substituted with one or more $R^4$ independently; $C_5$–$C_{10}$ cycloalkenyl optionally substituted with one or more $R^4$ independently; aryl optionally substituted with one or more $R^5$ independently; or heteroaryl optionally substituted with one or more $R^5$ independently;

$R^3$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$-alkynyl optionally substituted with one or more $R^4$ independently; $C_3$–$C_{10}$ cycloalkyl optionally substituted with one or more $R^4$ independently; $C_5$–$C_{10}$ cycloalkenyl optionally substituted with one or more $R^4$ independently; aryl optionally substituted with one or more $R^5$ independently and/or fused to a $C_3$–$C_{10}$ cycloalkane; or heteroaryl optionally substituted with one or more $R^5$ independently and/or fused to a $C_3$–$C_{10}$ cycloalkane;

$R^2$ may be connected to $R^3$ by a saturated or unsaturated bridge containing 1–3 carbon atoms, nitrogen atoms, oxygen atoms or sulphur atoms independently, or a valence bond, thus forming a ring, said ring may be fused to an aryl or heteroaryl, optionally substituted by one or more $R^5$ independently;

$R^4$ is cycloalkyl, aryl optionally substituted with one or more $R^5$ independently; heteroaryl optionally substituted with one or more $R^5$ independently; amino optionally substituted with one or more $R^6$ independently; —SO—$R^6$; —SO$_2$—$R^6$; —CO—$R^6$; —COO—$R^6$, —CONH—$R^6$; —CON($R^6$)$_2$; —O—$R^6$; —S—$R^6$; carboxy; acetamido; cyano; nitro; halogen; hydroxy; trifluoromethyl; trifluoromethoxy; sulfamoyl; carbamoyl; hydroxymethyl;

$R^5$ is halogen, $C_1$–$C_{10}$ alkyl, $C_1$–$C_{10}$ alkoxy, $C_1$–$C_{10}$ alkylamino, $C_1$–$C_{10}$ dialkylamino benzyl, benzyloxy, hydroxymethyl, nitro, trifluoromethyl, trifluoromethoxy, trifluoromethylthio, N-hydroxyimino, cyano; carboxy; acetamido; hydroxy; sulfamoyl, carbamoyl;

$R^6$ is $C_1$–$C_{10}$ alkyl, $C_2$–$C_{10}$ alkenyl, $C_2$–$C_{10}$-alkynyl, $C_3$–$C_{10}$-cycloalkyl, $C_5$–$C_{10}$ cycloalkenyl where any one of said alkyl, alkenyl, alkynyl, cycloalkyl, or cykloalkenyl may optionally be substituted with aryl optionally substituted with one or more $R^5$ independently or heteroaryl optionally substituted with one or more $R^5$ independently; benzyl, phenethyl; aryl optionally substituted with one or more $R^5$ independently; or heteroaryl optionally substituted with one or more $R^5$ independently with the proviso that $R^2$ and $R^3$ cannot both be H;

or a salt thereof with a pharmaceutically acceptable acid or base.

In a preferred embodiment the invention provides compounds of formula III

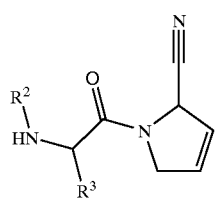

Formula III wherein $R^2$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$-alkynyl optionally substituted with one or more $R^4$ independently; $C_3$–$C_{10}$-cycloalkyl optionally substituted with one or more $R^4$ independently; $C_5$–$C_{10}$ cycloalkenyl optionally substituted with one or more $R^4$ independently; aryl optionally substituted with one or more $R^5$ independently; or heteroaryl optionally substituted with one or more $R^5$ independently;

$R^3$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$-alkynyl optionally substituted with one or more $R^4$ independently; $C_3$–$C_{10}$ cycloalkyl optionally substituted with one or more $R^4$ independently; $C_5$–$C_{10}$ cycloalkenyl optionally substituted with one or more $R^4$ independently; aryl optionally substituted with one or more $R^5$ independently and/or fused to a $C_3$–$C_{10}$ cycloalkane; or heteroaryl optionally substituted with one or more $R^5$ independently and/or fused to a $C_3$–$C_{10}$ cycloalkane;

$R^2$ may be connected to $R^3$ by a saturated or unsaturated bridge containing 1–3 carbon atoms, nitrogen atoms, oxygen atoms, or sulphur atoms independently, or a valence bond, thus forming a ring, said ring may be fused to an aryl or heteroaryl, optionally substituted by one or more $R^5$ independently;

$R^4$ is cycloalkyl, aryl optionally substituted with one or more $R^5$ independently; heteroaryl optionally substituted with one or more $R^5$ independently; amino optionally substituted with one or more $R^6$ independently; $-SO-R^6$; $-SO_2-R^6$; $-CO-R^6$; $-COO-R^6$, $-CONH-R^6$; $-CON(R^6)_2$; $-O-R^6$; $-S-R^6$; carboxy; acetamido; cyano; nitro; halogen; hydroxy; trifluoromethyl; trifluoromethoxy; sulfamoyl; carbamoyl; hydroxymethyl;

$R^5$ is halogen, $C_1-C_{10}$ alkyl, $C_1-C_{10}$ alkoxy, $C_1-C_{10}$ alkylamino, $C_1-C_{10}$ dialkylamino benzyl, benzyloxy, hydroxymethyl, nitro, trifluoromethyl, trifluoromethoxy, trifluoromethylthio, N-hydroxyimino, cyano; carboxy; acetamido; hydroxy; sulfamoyl, carbamoyl;

$R_6$ is $C_1-C_{10}$ alkyl, $C_2-C_{10}$ alkenyl, $C_2-C_{10}$-alkynyl, $C_3-C_{10}$-cycloalkyl, $C_5-C_{10}$ cycloalkenyl where any one of said alkyl, alkenyl, alkynyl, cycloalkyl, or cykloalkenyl may optionally be substituted with aryl optionally substituted with one or more $R^5$ independently or heteroaryl optionally substituted with one or more $R^5$ independently; benzyl, phenethyl; aryl optionally substituted with one or more $R^5$ independently; or heteroaryl optionally substituted with one or more $R^5$ independently with the proviso that $R^2$ and $R^3$ cannot both be H;

or a salt thereof with a pharmaceutically acceptable acid or base.

In another preferred embodiment, the invention provides compounds of formula

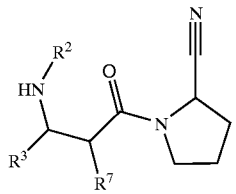

Formula IV wherein at least one of the bonds in the five-membered ring is a double bond;

$R^2$ is H; $C_1-C_{10}$ alkyl optionally substituted with one or more $R^4$ independently; $C_2-C_{10}$ alkenyl optionally substituted with one or more $R^4$ independently; $C_2-C_{10}$-alkynyl optionally substituted with one or more $R^4$ independently; $C_3-C_{10}$-cycloalkyl optionally substituted with one or more $R^4$ independently; $C_5-C_{10}$ cycloalkenyl optionally substituted with one or more $R^4$ independently; aryl optionally substituted with one or more $R^5$ independently; or heteroaryl optionally substituted with one or more $R^5$ independently;

$R^3$ is H; $C_1-C_{10}$ alkyl optionally substituted with one or more $R^4$ independently; $C_2-C_{10}$ alkenyl optionally substituted with one or more $R^4$ independently; $C_2-C_{10}$-alkynyl optionally substituted with one or more $R^4$ independently; $C_3-C_{10}$ cycloalkyl optionally substituted with one or more $R^4$ independently; $C_5-C_{10}$ cycloalkenyl optionally substituted with one or more $R^4$ independently; aryl optionally substituted with one or more $R^5$ independently and/or fused to a $C_3-C_{10}$ cycloalkane; or heteroaryl optionally substituted with one or more $R^5$ independently and/or fused to a $C_3-C_{10}$ cycloalkane;

$R^2$ may be connected to $R^3$ or $R^7$ by a saturated or unsaturated bridge containing 1–3 carbon atoms, nitrogen atoms, oxygen atoms, sulphur atoms independently, or a valence bond, thus forming a ring, said ring may be fused to an aryl or heteroaryl, optionally substituted by one or more $R^5$ independently;

$R^4$ is cycloalkyl; aryl optionally substituted with one or more $R^5$ independently; heteroaryl optionally substituted with one or more $R^5$ independently; amino optionally substituted with one or more $R^6$ independently; $-SO-R^6$; $-SO_2-R^6$; $-CO-R^6$; $-COO-R^6$, $-CONH-R^6$; $-CON(R^6)_2$; $-O-R^6$; $-S-R^6$; carboxy; acetamido; cyano; nitro; halogen; hydroxy; trifluoromethyl; trifluoromethoxy; sulfamoyl; carbamoyl; hydroxymethyl;

$R^5$ is halogen, $C_1-C_{10}$ alkyl, $C_1-C_{10}$ alkoxy, $C_1-C_{10}$ alkylamino, $C_1-C_{10}$ dialkylamino benzyl, benzyloxy, hydroxymethyl, nitro, trifluoromethyl, trifluoromethoxy, trifluoromethylthio, N-hydroxyimino, cyano; carboxy; acetamido; hydroxy; sulfamoyl, carbamoyl;

$R^6$ is $C_1-C_{10}$ alkyl, $C_2-C_{10}$ alkenyl, $C_2-C_{10}$-alkynyl, $C_3-C_{10}$-cycloalkyl, $C_5-C_{10}$ cycloalkenyl where any one of said alkyl, alkenyl, alkynyl, cycloalkyl, or cykloalkenyl may optionally be substituted with aryl optionally substituted with one or more $R^5$ independently or heteroaryl optionally substituted with one or more $R^5$ independently; benzyl, phenethyl; aryl optionally substituted with one or more $R^5$ independently; or heteroaryl optionally substituted with one or more $R^5$ independently;

$R^7$ is H; $C_1-C_{10}$ alkyl optionally substituted with one or more $R^4$ independently; $C_2-C_{10}$ alkenyl optionally substituted with one or more $R^4$ independently; $C_2-C_{10}$-alkynyl optionally substituted with one or more $R^4$ independently; $C_3-C_{10}$-cycloalkyl optionally substituted with one or more $R^4$ independently; $C_5-C_{10}$-cycloalkenyl optionally substituted with one or more $R^4$ independently; aryl optionally substituted with one or more $R^5$ independently; heteroaryl optionally substituted with one or more $R^5$ independently, halogen, $C_1-C_{10}$ alkoxy, $C_1-C_{10}$ alkylthio, $C_1-C_{10}$ alkylamino, $C_1-C_{10}$ dialkylamino, hydroxymethyl, nitro, trifluoromethyl, trifluoromethoxy, trifluoromethylthio, N-hydroxyimino, cyano; carboxy; acetamido; hydroxy; sulfamoyl, carbamoyl;

with the proviso that the groups $R^2$, $R^3$, and $R^7$ cannot all be H.

or a salt thereof with a pharmaceutically acceptable acid or base.

In another preferred embodiment, the invention provides compounds of formula V

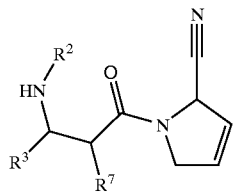

Formula V wherein $R^2$ is H; $C_1-C_{10}$ alkyl optionally substituted with one or more $R^4$ independently; $C_2-C_{10}$ alkenyl optionally substituted with one or more $R^4$ independently; $C_2-C_{10}$-alkynyl optionally substituted with one or more $R^4$ independently; $C_3$–$C_{10}$-cycloalkyl optionally substituted with one or more $R^4$ independently; $C_5$–$C_{10}$ cycloalkenyl optionally substituted with one or more $R^4$ independently; aryl optionally substituted with one or more $R^5$ independently; or heteroaryl optionally substituted with one or more $R^5$ independently;

$R^3$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$-alkynyl optionally substituted with one or more $R^4$ independently; $C_3$–$C_{10}$ cycloalkyl optionally substituted with one or more $R^4$ independently; $C_5$–$C_{10}$ cycloalkenyl optionally substituted with one or more $R^4$ independently; aryl optionally substituted with one or more $R^5$ independently and/or fused to a $C_3$–$C_{10}$ cycloalkane; or heteroaryl optionally substituted with one or more $R^5$ independently and/or fused to a $C_3$–$C_{10}$ cycloalkane;

$R^2$ may be connected to $R^3$ or $R^7$ by a saturated or unsaturated bridge containing 1–3 carbon atoms, nitrogen atoms, oxygen atoms, or sulphur atoms independently, or a valence bond, thus forming a ring, said ring may be fused to an aryl or heteroaryl, optionally substituted by one or more $R^5$ independently;

$R^4$ is cycloalkyl; aryl optionally substituted with one or more $R^5$ independently; heteroaryl optionally substituted with one or more $R^5$ independently; amino optionally substituted with one or more $R^6$ independently; —SO—$R^6$; —SO$_2$—$R^6$; —CO—$R^6$; —COO—$R^6$, —CONH—$R^6$; —CON($R^6$)$_2$; —O—$R^6$; —S—$R^6$; carboxy; acetamido; cyano; nitro; halogen; hydroxy; trifluoromethyl; trifluoromethoxy; sulfamoyl; carbamoyl; hydroxymethyl;

$R^5$ is halogen, $C_1$–$C_{10}$ alkyl, $C_1$–$C_{10}$ alkoxy, $C_1$–$C_{10}$ alkylamino, $C_1$–$C_{10}$ dialkylamino, benzyl, benzyloxy, hydroxymethyl, nitro, trifluoromethyl, trifluoromethoxy, trifluoromethylthio, N-hydroxyimino, cyano; carboxy; acetamido; hydroxy; sulfamoyl, carbamoyl;

$R^6$ is $C_1$–$C_{10}$ alkyl, $C_2$–$C_{10}$ alkenyl, $C_2$–$C_{10}$-alkynyl, $C_3$–$C_{10}$-cycloalkyl, $C_5$–$C_{10}$ cycloalkenyl where any one of said alkyl, alkenyl, alkynyl, cycloalkyl, or cykloalkenyl may optionally be substituted with aryl optionally substituted with one or more $R^5$ independently or heteroaryl optionally substituted with one or more $R^5$ independently; benzyl, phenethyl; aryl optionally substituted with one or more $R^5$ independently; or heteroaryl optionally substituted with one or more $R^5$ independently $R^7$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$-alkynyl optionally substituted with one or more $R^4$ independently; $C_3$–$C_{10}$-cycloalkyl optionally substituted with one or more $R^4$ independently; $C_5$–$C_{10}$ cycloalkenyl optionally substituted with one or more $R^4$ independently; aryl optionally substituted with one or more $R^5$ independently; heteroaryl optionally substituted with one or more $R^5$ independently, halogen, $C_1$–$C_{10}$ alkoxy, $C_1$–$C_{10}$ alkylthio, $C_1$–$C_{10}$ alkylamino, $C_1$–$C_{10}$ dialkylamino, hydroxymethyl, nitro, trifluoromethyl, trifluoromethoxy, trifluoromethylthio, N-hydroxyimino cyano; carboxy; acetamido; hydroxy; sulfamoyl, carbamoyl;

with the proviso that the groups $R^2$, $R^3$, and $R^7$ cannot all be H.

or a salt thereof with a pharmaceutically acceptable acid or base.

A further preferred embodiment is represented by the compounds of the invention wherein:

$R^2$ is H; $C_1$–$C_{10}$ alkyl optionally substituted with $R^4$; $C_2$–$C_{10}$ alkenyl optionally substituted with $R^4$; $C_2$–$C_{10}$-alkynyl optionally substituted with $R^4$; aryl optionally substituted with one or more $R^5$ independently; or heteroaryl optionally substituted with one or more $R_5$ independently;

$R^2$ may be connected to $R^3$ or $R^7$ by a saturated or unsaturated bridge containing 1–3 carbon atoms, nitrogen atoms, oxygen atoms, or sulphur atoms independently, or a valence bond, thus forming a ring, said ring may be fused to an aryl or heteroaryl, optionally substituted by one or more $R^5$ independently;

Another preferred embodiment is represented by the compounds of the invention wherein $R^2$ is H or $C_1$–$C_{10}$ alkyl optionally substituted with $R^4$.

Another preferred embodiment is represented by the compounds of the invention wherein $R^2$ is H.

Another preferred embodiment is represented by the compounds of the invention wherein:

$R^3$ is H; $C_1$–$C_{10}$ alkyl optionally substituted with $R^4$; $C_2$–$C_{10}$ alkenyl optionally substituted with $R^4$; $C_2$–$C_{10}$-alkynyl optionally substituted with $R^4$; $C_3$–$C_{10}$ cycloalkyl optionally substituted with $R^4$; aryl optionally substituted with one or more $R^5$ independently and/or fused to a $C_3$–$C_{10}$ cycloalkane; or heteroaryl optionally substituted with one or more $R^5$ independently and/or fused to a $C_3$–$C_{10}$ cycloalkane;

Another preferred embodiment is represented by the compounds of the invention wherein:

$R^3$ is H; $C_1$–$C_{10}$ alkyl optionally substituted with $R^4$; or aryl optionally substituted with one or more $R^5$ independently and/or fused to a $C_3$–$C_{10}$ cycloalkane.

Another preferred embodiment is represented by the compounds of the invention wherein $R^3$ is $C_1$–$C_{10}$ alkyl optionally substituted with $R^4$.

Another preferred embodiment is represented by the compounds of the invention wherein:

$R^4$ is cycloalkyl; aryl optionally substituted with one or more $R^5$ independently; heteroaryl optionally substituted with one or more $R^5$ independently; —SO—$R^6$; —SO$_2$—$R^6$; —CO—$R^6$; —COO—$R^6$; —O—$R^6$; —S—$R^6$;

Another preferred embodiment is represented by the compounds of the invention wherein:

$R^4$ is aryl optionally substituted with one or more $R^5$ independently; heteroaryl optionally substituted with one or more $R^5$ independently; —CO—$R^6$; —COO—$R^6$; —O—$R^6$; —S—$R^6$;

Another preferred embodiment is represented by the compounds of the invention wherein $R^4$ is aryl optionally substituted with one or more $R^5$ independently;

Another preferred embodiment is represented by the compounds of the invention wherein $R^4$ is —COO—$R^6$, —O—$R^6$, or —S—$R^6$;

Another preferred embodiment is represented by the compounds of the invention wherein $R^5$ is halogen, $C_1$–$C_{10}$ alkyl, $C_1$–$C_{10}$ alkoxy, $C_1$–$C_{10}$ alkylamino, $C_1$–$C_{10}$ dialkylamino, benzyl, or benzyloxy.

Another preferred embodiment is represented by the compounds of the invention wherein $R^5$ is halogen, $C_1$–$C_{10}$ alkyl, or $C_1$–$C_{10}$ alkoxy.

Another preferred embodiment is represented by the compounds of the invention wherein $R^6$ is $C_1$–$C_{10}$ alkyl, $C_2$–$C_{10}$ alkenyl optionally substituted with $R^4$; $C_2$–$C_{10}$-alkynyl optionally substituted with $R^4$; benzyl, aryl optionally substituted with one or more $R^5$ independently, or heteroaryl optionally substituted with one or more $R^5$ independently.

Another preferred embodiment is represented by the compounds of the invention wherein $R^6$ is $C_1$–$C_{10}$ alkyl, benzyl, or aryl optionally substituted with one or more $R^5$ independently.

The most preferred compounds of formula I wherein B represents an alpha-amino acid are the following:

(S,S) 1-(2-Amino-propionyl)-2,5-dihydro-1H-pyrrole-2-carbonitrile
(S,S) 1-(2-Amino-butyryl)-2,5-dihydro-1H-pyrrole-2-carbonitrile
(S,S) 1-(2-Amino-3-methyl-butyryl)-2,5-dihydro-1H-pyrrole-2-carbonitrile
(S,S) 1-(2-Amino-3,3-dimethyl-butyryl)-2,5-dihydro-1H-pyrrole-2-carbonitrile
(S,S) 1-(2-Amino-4-methyl-pent-4-enoyl)-2,5-dihydro-1H-pyrrole-2-carbonitrile
(S,S) 1-(2-Amino-3,3-diethyl-pentanoyl)-2,5-dihydro-1H-pyrrole-2-carbonitrile
(S,S) 1-(2-Amino-2-cyclopentylacetyl)-2,5-dihydro-1H-pyrrole-2-carbonitrile
(S,S) 1-(2-Amino-2-cyclohexylacetyl)-2,5-dihydro-1H-pyrrole-2-carbonitrile
(S,S) 1-(2-Amino-2-cycloheptylacetyl)-2,5-dihydro-1H-pyrrole-2-carbonitrile
(S,S) 1-(2-Amino-2-bicyclo[2.2.2]oct-1-yl-acetyl)-2,5-dihydro-1H-pyrrole-2-carbonitrile
(S,S) 1-(2-Adamantan-1-yl-2-amino-acetyl)-2,5-dihydro-1H-pyrrole-2-carbonitrile
(S,S) 1-(2-Amino-2-phenylacetyl)-2,5-dihydro-1H-pyrrole-2-carbonitrile
(S,S) 1-(2-Amino-2-(2,6 dimethylphenyl)acetyl)-2,5-dihydro-1H-pyrrole-2-carbonitrile
(S,S) 1-(2-Amino-3,3-diphenyl-propionyl)-2,5-dihydro-1H-pyrrole-2-carbonitrile
(S,S) 1-(2-Amino-(3(R)-methylpentanoyl)-2,5-dihydro-1H-pyrrole-2-carbonitrile
(S,S) 1-(2-Amino-(4-methylpentanoyl)-2,5-dihydro-1H-pyrrole-2-carbonitrile
(S,S) 1-(2,6-Diamino-hexanoyl)-2,5-dihydro-1H-pyrrole-2-carbonitrile
(S,S) 1-(2-Amino-6-dibenzylamino-hexanoyl)-2,5-dihydro-1H-pyrrole-2-carbonitrile
(S,S) 1-(2-Amino-6-benzylamino-hexanoyl)-2,5-dihydro-1H-pyrrole-2-carbonitrile
(S,S) [5-Amino-6-(2-cyano-2,5-dihydro-pyrrol-1-yl)-6-oxo-hexyl]-carbamic acid-tert-butyl ester
(S,S) [5-Amino-6-(2-cyano-2,5-dihydro-pyrrol-1-yl)-6-oxo-hexyl]-carbamic acid 9-H-fluoren-9-ylmethyl ester
(S,S) 4-Amino-5-(2-cyano-2,5-dihydro-pyrrol-1-yl)-5-oxo-pentanoic acid amide
(S,S) 4-Amino-5-(2-cyano-2,5-dihydro-pyrrol-1-yl)-5-oxo-pentanoic acid benzylamide
(S,S) 4-Amino-5-(2-cyano-2,5-dihydro-pyrrol-1-yl)-5-oxo-pentanoic acid benzyl ester
(S,S) 4-Amino-5-(2-cyano-2,5-dihydro-pyrrol-1-yl)-5-oxo-pentanoic acid-tert-butyl ester
(S,S) 1-(2-Amino-3-benzyloxy-propionyl)-2,5-dihydro-1H-pyrrole-2-carbonitrile
(S,S) 1-(2-Amino-(4-methylsulfanyl-butyryl)-2,5-dihydro-1H-pyrrole-2-carbonitrile
(S,S) 1-(2-Amino-(3-phenylpropionyl)-2,5-dihydro-1H-pyrrole-2-carbonitrile
(S,S) 1-(Pyrrolidine-2-carbonyl)-2,5-dihydro-1H-pyrrole-2-carbonitrile
(S,S) 6-{2-[2-(2-Cyano-2,5-dihydro-pyrrol-1-yl)-2-oxo-ethylamino]-ethylamino}-nicotino-nitrile
(S,S) 1-{2-[2-(5-Chloro-pyridin-2-ylamino)-ethylamino]-acetyl}-2,5-dihydro-1H-pyrrole-2 carbonitrile
(S,S) 1-{2-[2-(5-Trifluoromethyl-pyridin-2-ylamino)-ethylamino]-acetyl}-2,5-dihydro-1H-pyrrole-2-carbonitrile
(S,S) 1-[2-(1-Hydroxymethyl-cyclopentylamino)-acetyl]-2,5-dihydro-1H-pyrrole-2-carbonitrile
(S,S) 1-{2-[2-(5-Nitro-pyridin-2-ylamino)-ethylamino] acetyl}-2,5-dihydro-1H-pyrrole-2carbonitrile, and
(S,S) 1-[2-(3-Isopropoxy-propylamino)-acetyl]-2,5-dihydro-1H-pyrrole-2-carbonitrile.

The most preferred compounds of formula I wherein B represents a beta-amino acid are the following:

1-(Piperidine-3-carbonyl)-2,5-dihydro-1-H-pyrrole-2-S-carbonitrile 1-(cis(2-Amino-cyclopenanecarbonyl))-2,5-dihydro-1-H-pyrrole-2-S-carbonitrile 1-(3-R-Amino-5-phenyl-pentanoyl)-2,5-dihydro-1-H-pyrrole-2-S-carbonitrile 1-(3-S-Amino-5-phenyl-pentanoyl)-2,5-dihydro-1-H-pyrrole-2-S-carbonitrile 1-(3-S-Amino-4-phenyl-butyryl)-2,5-dihydro-1-H-pyrrole-2-S-carbonitrile 1-(3-R-Amino-3-phenyl-propionyl)-2,5-dihydro-1-H-pyrrole-2-S-carbonitrile 1-(Morpholine-2-carbonyl)-2,5-dihydro-1-H-pyrrole-2-S-carbonitrile 1-(3-R-Amino-6-phenyl-hex-5-enoyl)-2,5-dihydro-1-H-pyrrole-2-S-carbonitrile 1-(3-R-Amino4-benzo[b]thiophen-2-yl-butyryl)-2,5-dihydro-1-H-pyrrole-2-S-carbonitrile 1-(3-R-amino-4-pyridin-3-yl-butyryl)-2,5-dihydro-1-H-pyrrole-2-S-carbonitrile 1-[3-S-Amino-4-(4-benzyloxy-phenyl)-butyryl]-2,5-dihydro-1-H-pyrrole-2-S-carbonitrile 1-[2-S-Pyrolidin-2-yl-acetyl)-2,5-dihydro-1-H-pyrrole-2-S-carbonitrile 1-[4-(2-Chloro-phenyl)-pyrrolidine-3-carbonyl]-2,5-dihydro-1-H-pyrrole-2-S-carbonitrile 1-(4-R-Phenyl-pyrrolidine-3-S-carbonyl)-2,5-dihydro-1-H-pyrrole-2-S-carbonitrile or a salt thereof with a pharmaceutically acceptable acid or base.

The invention also relates to methods for preparing the above-mentioned compounds. These methods comprise (1) and (2) described below:

(1) Reacting an alpha amino acid or a beta-amino acid, suitably amino-protected with a standard protecting group such as Boc-, Fmoc-, CBz- or the like, with a 2-carbamoyl substituted unsaturated heterocyclic compound of formula VI,

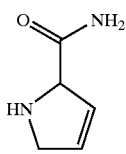

Formula VI under standard peptide coupling conditions to give an amide product; dehydrating the carbamoyl functionality of this material using standard dehydrating agents such as phosphorous oxycloride in pyridine or DMF, or trifluoroacetic acid anhydride, or the bromine/triphenylphospine adduct to give the nitrile, and to deprotect the amino group using standard chemical transformations to give the compounds of the invention.

(2) Reacting a 2-carbamoyl substituted unsaturated heterocyclic compound of formula VI,

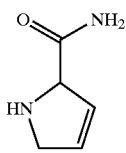

Formula VI with an alpha-halogenated carboxylic acid chloride, bromide, or anhydride to give compound of formula VII,

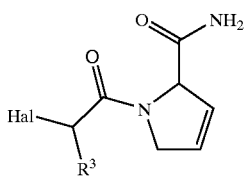

Formula VII dehydrating the carbamoyl functionality of this material using standard dehydrating agents such as phosphorous oxycloride in pyridine or DMF, or trifluoroacetic acid anhydride, or the bromine/triphenylphospine adduct to give the nitrile, and reacting the nitrile compound with an appropriately substituted amine to give the compounds of the invention.

The compounds of the present invention may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in Journal of Pharmaceutical Science, 66, 2 (1977) which are known to the skilled artisan.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of this invention may form solvates with standard low molecular weight solvents using methods known to the skilled artisan.

It is to be understood that the invention extends to all of the stereo isomeric forms of the claimed compounds, as well as the racemates.

A further aspect of the invention is the use of a compound of the invention for the manufacture of a medicament for treating a condition that may be regulated or normalized via inhibition of DPP-IV.

Another aspect of the invention is the use of a compound of the invention for the manufacture of a medicament for treatment of metabolic disorders.

Another aspect of the invention is the use of a compound of the invention for the manufacture of a medicament for blood glucose lowering.

Another aspect of the invention is the use of a compound of the invention for the manufacture of a medicament for treatment of type II diabetes Another aspect of the invention is the use of a compound of the invention for the manufacture of a medicament for the treatment of impaired glucose tolerance (IGT).

Another aspect of the invention is the use of a compound of the invention for the manufacture of a medicament for the treatment of impaired fasting glucose (IFG).

Another aspect of the invention is the use of a compound of the invention for the manufacture of a medicament for prevention of hyperglycemia.

Another aspect of the invention is the use of a compound of the invention for the manufacture of a medicament for delaying the progression of impaired glucose tolerance (IGT) to type II diabetes.

Another aspect of the invention is the use of a compound of the invention for the manufacture of a medicament for delaying the progression of non-insulin requiring type II diabetes to insulin requiring type II diabetes.

Another aspect of the invention is the use of a compound of the invention for the manufacture of a medicament for increasing the number and/or the size of beta cells in a mammalian subject.

Another aspect of the invention is the use of a compound of the invention for the manufacture of a medicament for treatment of beta cell degeneration, in particular apoptosis of beta cells.

Another aspect of the invention is the use of a compound of the invention for the manufacture of a medicament for the treatment of disorders of food intake.

Another aspect of the invention is the use of a compound of the invention for the manufacture of a medicament for the treatment of obesity.

Another aspect of the invention is the use of a compound of the invention for the manufacture of a medicament for appetite regulation or induction of satiety.

Another aspect of the invention is the use of a compound of the invention for the manufacture of a medicament for the treatment of dyslipidemia.

Another aspect of the invention is the use of a compound of the invention for the manufacture of a medicament for treatment of functional dyspepsia, in particular irritable bowel syndrome.

A further aspect of the invention is a method for treating the conditions mentioned above by administering to a subject in need thereof an effective amount of a compound of the invention.

Combination Treatments

The invention furthermore relates to the use of a compound according to the present invention for the preparation of a medicament for use in the treatment of diabetes in a regimen that additionally comprises treatment with another antidiabetic agent.

In one embodiment of this invention, the antidiabetic agent is insulin or GLP-1 or any analogue or derivative thereof.

In another embodiment the antidiabetic agent is a non-peptidyl hypoglycemic agent, preferably an oral hypoglycemic agent.

Oral hypoglycemic agents are preferably selected from the group consisting of sulfonylureas, non-sulphonylurea insulin secretagogues, biguanides, thiazolidinediones, alpha glucosidase inhibitors, glucagon antagonists, GLP-1 agonists, potassium channel openers, insulin sensitizers, hepatic enzyme inhibitors, glucose uptake modulators, compounds modifying the lipid metabolism, compounds lowering food intake, and agents acting on the ATP-dependent potassium channel of the β-cells.

Among the sulfonylureas, tolbutamide, glibenclamide, glipizide and gliclazide are preferred.

Among the non-sulphonylurea insulin secretagogues, repaglinide and nateglinide are preferred.

Among the biguanides, metformin is preferred.

Among the thiazolidinediones, troglitazone, rosiglitazone and ciglitazone are preferred.

Among the glucosidase inhibitors, acarbose is preferred.

Among the agents acting on the ATP-dependent potassium channel of the β-cells the following are preferred: glibenclamide, glipizide, gliclazide, repaglinide.

Pharmaceutical Compositions

In another aspect, the present invention includes within its scope pharmaceutical compositions comprising, as an active ingredient, at least one compound of the invention which inhibits the enzymatic activity of DPP-IV or a pharmaceutically acceptable salt or prodrug or hydrate thereof together with a pharmaceutically acceptable carrier or diluent.

Pharmaceutical compositions containing a compound of the invention of the present invention may be prepared by conventional techniques, e.g. as described in *Remington: The Science and Practise of Pharmacy*, 19$^{th}$ Ed., 1995. The compositions may appear in conventional forms, for example capsules, tablets, aerosols, solutions, suspensions or topical applications.

Typical compositions include a compound of the invention which inhibits the enzymatic activity of DPP-IV or a pharmaceutically acceptable basic addition salt or prodrug or hydrate thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material that acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

The route of administration may be any route, which effectively transports the active compound of the invention which inhibits the enzymatic activity of DPP-IV to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the invention which inhibits the enzymatic activity of DPP-IV, dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that may be prepared by conventional tabletting techniques may contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |

-continued

| Coating: | |
|---|---|
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of the various diseases as mentioned above, e.g., type II diabetes, IGT, IFG, obesity, appetite regulation or as a blood glucose lowering agent, and especially type II diabetes. Such mammals include also animals, both domestic animals, e.g. household pets, and non-domestic animals such as wildlife.

The compounds of the invention are effective over a wide dosage range. For example, in the treatment of adult humans, dosages from about 0.05 to about 1000 mg, preferably from about 0.1 to about 500 mg, per day may be used. A most preferable dosage is about 0.5 mg to about 250 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.05 to about 1000 mg of active ingredient together with a pharmaceutically acceptable carrier per unit dosage.

Usually, dosage forms suitable for oral, nasal, pulmonal or transdermal administration comprise from about 0.05 mg to about 1000 mg, preferably from about 0.5 mg to about 250 mg of the compounds admixed with a pharmaceutically acceptable carrier or diluent.

The invention also encompasses prodrugs of a compound of the invention which on administration undergo chemical conversion by metabolic processes before becoming active pharmacological substances. In general, such prodrugs will be functional derivatives of a compound of the invention which are readily convertible in vivo into a compound of the invention. Conventional procedures for the selection and preparation of suitable prodrug derivatives are described, for example, in "Design of Prodrugs", ed. H. Bundgaard, Elsevier, 1985.

The invention also encompasses active metabolites of a compound of the invention.

Methods for Measuring the Activity of Compounds which Inhibit the Enzymatic Activity of CD26/DPP-IV Summary Chemical compounds are tested for their ability to inhibit the enzyme activity of purified CD26/DPP-IV. Briefly, the activity of CD26/DPP-IV is measured in vitro by its ability to cleave the synthetic substrate Gly-Pro-p-nitroanilide (Gly-Pro-pNA). Cleavage of Gly-Pro-pNA by DPP-IV liberates the product p-nitroanilide (pNA), whose rate of appearance is directly proportional to the enzyme activity. Inhibition of the enzyme activity by specific enzyme inhibitors slows down the generation of pNA. Stronger interaction between an inhibitor and the enzyme results in a slower rate of generation of pNA. Thus, the degree of inhibition of the rate of accumulation of pNA is a direct measure of the strength of enzyme inhibition. The accumulation of pNA is measured spectrophotometrically. The inhibition constant, Ki, for each compound is determined by incubating fixed amounts of enzyme with several different concentrations of inhibitor and substrate.

Materials:

The following reagents and cells are commercially available:

Porcine CD26/DPP-IV (Sigma D-7052), Gly-Pro-pNA (Sigma G0513).

Assay buffer: 50 mM Tris pH7.4, 150 mM NaCl, 0,1% Triton X-100.

Gly-Pro-pNA cleavage-assay for CD26:

The activity of purified CD26/DPP-IV is assayed in reactions containing:

70 ul assay buffer 10 ul inhibitor or buffer 10 ul substrate (Gly-Pro-pNA from a 0.1M stock solution in water) or buffer 10 ul enzyme or buffer Reactions containing identical amounts of enzyme, but varying concentrations of inhibitor and substrate, or buffer as control, are set up in parallel in individual wells of a 96-well ELISA plate. The plate is incubated at 25° C. and absorbance is read at 405 nm after 60 min incubation. The inhibitor constants are calculated by nonlinear regression hyperbolic fit and the result is expressed as inhibition constant (Ki) in nM.

Diabetes Model

The Zucker Diabetic Fatty (ZDF) rat model can be used to investigate the effects of the compounds of the invention on both the treatment and prevention of diabetes as rats of this sub-strain are initially pre-diabetic although develop severe type 2 diabetes characterized by increased HbA1c levels over a period of 6 weeks. The same strain can be used to predict the clinical efficacy of other anti-diabetic drug types. For example, the model predicts the potency and limited clinical efficacy of thiazolidinedione insulin sensitizer compounds.

EXAMPLES

A further detailed description of the invention is given with reference to the following examples.

Example 1

(S,S) 1-(2-Amino-3,3-dimethyl-butyryl)-2,5-dihydro-1H-pyrrole-2-carbonitrile (1)

(S)-2-Amino-N-tert-butyloxycarbonyl-3,3-dimethylbutyric acid (308 mg, 1.33 mmol) was dissolved in 3 ml of dichloromethane and 1-hydroxy-7-azabenzotriazole (HOAT) (180 mg, 1.33 mmol) and 1-ethyl-3-(3-dimethylaminopropyl)-carbodiimide, hydrochloride (EDAC) (258 mg, 1.35 mmol) was added. The mixture was stirred at room temperature for 30 minutes, and then (S) 2,5-dihydro-1H-pyrrole-2-carboxylic acid amide, (150 mg, 1.33 mmol) and diisopropylethylamine (0.46 ml, 2.68 mmol) were added. The reaction mixture was stirred at room temperature for 20 hours. The solvent was evaporated and the crude product was purified by preparative HPLC, using acetonitrile/water as the eluent. Fractions containing the product were collected and the solvents were evaporated, to afford 200 mg of (S,S) [1-(2-Carbamoyl-2,5-dihydro-pyrrole-1-carbonyl)-2,2-dimethyl-propyl]-carbamic acid tert-butyl ester (2). Oil, 47% yield. $^1$H-NMR (CDCl$_3$, 200 MHz) δ: 1.03 (s, 9H); 1.42 (s, 9H); 4.29 (d, 1H); 4.36–4.50 (m, 1H); 4.62–4.73 (m, 1H); 5.25–5.33 (m, 2H); 5.85–6.00 (m, 3H); 6.88 (br. s, 1H).

(175 mg, 0.54 mmol) of (2) was dissolved in 4 ml of pyridine and the mixture was cooled to 0° C. Phosphorus oxychloride (0.2 ml, 2.15 mmol) was added dropwise and after 10 minutes of stirring the reaction mixture was poured into 20 ml of ice water and the organic material was extracted into 5×10 ml of ethyl acetate. The combined organic extract was washed with 2×20 ml of water, 1×20 ml of brine and dried over magnesium sulphate. The solvent was evaporated to afford 140 mg of (S,S) [1-(2-Cyano-2,5-dihydro-pyrrole-1-carbonyl)-2,2-dimethyl-propyl]-carbamic acid tert-butyl ester (3). Oil, 85% yield. $^1$H-NMR (CDCl$_3$, 200 MHz) δ: 1.05 (s, 9H); 1.42 (s, 9H); 4.22 (d, 1H); 4.39–4.53 (m, 1H); 4.65–4.77 (m, 1H); 5.30 (d, 1H); 5.41–5.48 (m, 1H); 5.83–5.90 (m, 1H); 6.09–6.15 (m, 1H).

(140 mg, 0.46 mmol) of (3) was dissolved in 0.5 ml of dichloromethane and the mixture was cooled to 0° C. 0.5 ml of trifluoroacetic acid was added and the reaction mixture was stirred at 0° C. for 1 hour. The solvent was evaporated and the crude product was purified by preparative HPLC, using acetonitrile/water as the eluent. Fractions containing the product were collected and the solvent was evaporated, to afford 25 mg of the title compound (1) as the trifluoroacetic acid salt. Oil, 17% yield. $^1$H-NMR (MeOH, 200 MHz) δ: 1.20 (s, 9H); 4.08 (s, 1H); 4.46–4.70 (m, 2H); 5.56–5.62 (m, 1H); 5.95–6.02 (m, 1H); 6.22–6.29 (m, 1H). LC-MS, m/z: 208.4 (M+1)

The following compounds were prepared essentially by the route outlined in example 1; however, most compounds were also purified by preparative HPLC after the dehydration step.

(S,S) 1-(2-Amino-4-methyl-pent-4-enoyl)-2,5-dihydro-1H-pyrrole-2-carbonitrile (2)

(29 mg) LC-MS (EI), m/z; 206 (m+1). Prepared from (s) 2-tert-Butoxycarbonylamino-4-methyl-pent-4-enoic acid.

(S,S) 1-(Pyrrolidine-2-carbonyl)-2,5-dihydro-1H-pyrrole-2-carbonitrile (3)

(30 mg) 1H-NMR (CDCl3, 200 MHz) δ: 6.13 (d, 1H); 5.90 (d, 1H); 5.50 (s, 1H); 4.78 (s, 1H); 4.46 (m, 2H); 3.53 (s, 2H); 2.52 (s, 1H); 2.18 (m, 3H); 1.4 (m, 1H). LC-MS (EI), m/z: 192 (M+1). Prepared from N-Boc-proline.

(S,S) 1-(2-Amino-3-phenyl-propionyl)-2,5-dihydro-1H-pyrrole-2-carbonitrile (4)

(27 mg). 1H-NMR (CDCl3, 200 MHz) δ: 7.30 (m, 5H); 5.85 (dd, 1H); 5.70 (dd, 1H); 5.38 (m, 1H); 3.33 (dd, 1H); 4.2 (dd, 1H); 3.33, (dd, 1H); 3.15 (dd, 1H); 2.88 (dd, 1H); LC-MS (EI), m/z: 242 (M+1). Prepared from N-Boc-Phenylalanine.

(S,S) 1-(2-Amino-4-methyl-pentanoyl)-2,5-dihydro-1H-pyrrole-2-carbonitrile (5)

(66 mg); 1H-NMR (CDCl3, 200 MHz) δ: 6.17 (dd, 1H); 5.90 (dd, 1H); 5.50 (m, 1H); 4.63 (dd, 1H); 4.38–4.28 (dd, 1H); 4.28–4.15 (dd, 1H); 1.92–1.54 (m, 3H); 1.00 (d, 6H). LC-MS (EI), m/z: 208 (M+1). Prepared from N-Boc-Leucine.

(S,S) 1-[2-Amino-3-(4-methoxy-phenyl)-propionyl]-2,5-dihydro-1H-pyrrole-2-carbonitrile (6)

(61 mg) 1H-NMR (CDCl3, 200 MHz) δ: 7.15 (d, 2H); 6.76 (d, 2H); 5.85 (d, 1H); 5.68 (d, 1H); 5.30 (s, 1H); 4.38 (m, 1H); 4.25 (d, 1H); 3.73 (s, 3H); 3.32 (m, 1H); 3.12 (m, 2H). LC-MS (EI), m/z: 272 (M+1). Prepared from (S) 2-tert-Butoxycarbonylamino-3-(4-methox-phenyl)-propionic acid.

(2S) 1-(2'-Amino-2'-phenyl-acetyl)-2,5-dihydro-1H-pyrrole-2-carbonitrile (7)

(68 mg) 1H-NMR (CDCl3, 200 MHz) δ: 7.48 (m, 5H); 5.57 (d, 1H); 5.75 (d, 1H); 5.43 d, 1H); 5.37 (s, 1H); 4.50 (dd, 1H); 3.75 (dd, 1H). LC-MS(EI), m/z: 228 (M+1). Prepared from (S)-Phenylglycine.

(S,S) 1-(2-Amino-3-benzyloxy-propionyl)-2,5-dihydro-1H-pyrrole-2-carbonitrile (8)

(61 mg) 1H-NMR (CDCl3, 200 MHz) δ: 7.32 (m, 5H); 6.05 (dd, 1H); 5.82 (dd, 1H); 5.45 (dd, 1H); 4.68–4.42 (m, 4H); 4.15 (dd, 1H); 3.83 d, 2H). LC-MS(EI), m/z: 272 (M+1). Prepared from N-Boc-O-benzylserine.

(S,S) 1-(2-Amino-4-methylsulfanyl-butyryl)-2,5-dihydro-1H-pyrrole-2-carbonitrile (9)

(65 mg) 1H-NMR (CDCl3, 200 MHz) δ: 6.15 (dd, 1H); 5.88 (dd, 1H); 5.52 (m, 1H); 4.58 (dd, 2H); 4.40 (t, 1H); 2.65 (m, 2H); 2.22 (m, 2H); 2.15 (s, 3H) LC-MS(EI), m/z: 226 (M+1). Prepared from N-Boc-methionine.

(S,S) 1-(2-Amino-2-cyclohexyl-acetyl)-2,5-dihydro-1H-pyrrole-2-carbonitrile (10)

(116 mg) 1H-NMR (CDCl3, 200 MHz) δ: 6.09 (d, 1H); 5.83 (d, 1H); 5.55 (s, 1H); 4.62 (d, 1H); 4.35 (d, 1H); 4.07 (d, 1H); 1.80 (m, 6H); 1.2 (m, 5H). LC-MS(EI), m/z: 234 (M+1). Prepared from (S) N-Boc-cyclohexylglycine (2S,2'S,3'R) 1-(2'-Amino-3'-methyl-pentanoyl)-2,5-dihydro-1H-pyrrole-2-carbonitrile (11)

(46 mg) 1H-NMR (CDCl3, 200 MHz) δ: 6.15 d(1H); 5.38 (d, 1H); 5.53 (s, 1H); 4.62 (d, 1H); 4.35 (d, 1H); 4.19 (d, 1H) 1.96 (m, 1H); 1,60 (m, 1H); 1.38 (m, 1H); 1.1 (m, 6H). LC-MS(EI), m/z: 208 (M+1). Prepared from N-Boc-allo-isoleucine (2S) 1-(2'-Amino-2'-naphthalen-1-yl-acetyl)-2,5-dihydro-1H-pyrrole-2-carbonitrile (12)

(8 mg) 1H-NMR (CDCl3, 200 MHz) δ: 8.30 (d, 1H); 7.95 (t, 2H); 7.60 (m, 4H); 5.87 (m, 1H); 5.78 (m, 1H); 5.52 (m, ½H; 5.40 (m, ½H); 4.43 (m, 1H); 4.45 (m, 1H); 4.38 (m, 1H); 3.40 (m, 1H) LC-MS(EI), m/z: 277 (M). Prepared from (S) N-Boc-2-naphtylglycine (2S,2'S,3'S), 1-(2'-Amino-3'-methyl-pentanoyl)-2,5-dihydro-1H-pyrrole-2-carbonitrile (13)

(41 mg) 1H-NMR (CDCl3, 200 MHz) δ: 6.12 (dd, 1H); 5.85 (dd, 1H); 5.48 (dd, 1H); 4.62 (dd, 1H); 4.35 (m, 1H); 4.05 (d, 1H); 2.0 (m, 1H); 1.61 (m, 1H); 1.27 (m, 1H); 1.07 (d, 3H); 0.97 (t, 3H). LC-MS(EI), m/z: 208 (M+1). Prepared from N-Boc-isoleucine (S,S) 1-[2-Amino-3-(4-fluoro-phenyl)-propionyl]-2,5-dihydro-1H-pyrrole-2-carbonitrile (14)

(51 mg) 1H-NMR (CDCl3, 200 MHz) δ: 7.25 (m, 2H); 7.15 (m, 2H); 5.90 (m, 1H); 5.74 (m, 1H); 5.38 (m, 1H); 4.25

(m, 2H); 3.17 (m, 3H). LC-MS(EI), m/z: 260 (M+1). Prepared from N-Boc-p-fluorophenylglycine.

3-Amino-4-(2-cyano-2,5-dihydro-pyrrol-1-yl)-4-oxo-butyric acid methyl ester (15)

(21 mg) LC-MS(ES), m/z: 224 (M+1). 1H-NMR (MEOH, 200 MHz) δ: 6.23 (m, 1H); 5.95 (m, 1H); 5.53 (m, 1H); 4.55 (m, 3H); 3.75 (s, 3H); 3.72 (t, 1H); 3.18–2.79 (m, 3H)

(S,S) 1-(2-Amino-propionyl)-2,5-dihydro-1H-pyrrole-2-carbonitrile (16)

(13 mg) LC-MS(ES), m/z: 166 (M+1). 1H-NMR (MEOH, 200 MHz) δ: 6.25 (m, 1H); 5.98 (m, 1H); 5.54 (m, 1H); 4.50 (m, 2H); 4.27 (q, 1H); 1.57 (d, 3H).

3-Amino-4-(2-cyano-2,5-dihydro-pyrrol-1-yl)-4-oxo-butyric acid benzyl ester (17)

(33 mg) LC-MS(ES), m/z: 300 (M+1). 1H-NMR (MEOH, 200 MHz) δ: 7.36 (m, 5H); 6.19 (m, 1H); 5.95 (m, 1H); 5.52 (m, 1H); 5.20 (s, 2H); 4.63–4.42 (m, 3H); 3.35–2.97 (m, 2H).

4-Amino-5-(2-cyano-2,5-dihydro-pyrrol-1-yl)-5-oxo-pentanoic acid benzyl ester (18)

(39 mg) LC-MS(ES), m/z: 314 (M+1). 1H-NMR (MEOH, 200 MHz) δ: 7.35 (m, 5H); 6.20 m, 1H); 5.95 (m, 1H); 5.53 (m, 1H); 5.18 (s, 2H); 4.45 (m, 2H); 4.35 (dd, 1H); 2.63 (t, 2H); 2.23 (m, 2H).

1-(2-Amino-3,3-diphenyl-propionyl)-2,5-dihydro-1H-pyrrole-2-carbonitrile (19)

(1 mg) LC-MS(ES), m/z: 318 (M+1)

(2S,2'R) 1-(2-Amino-3-methyl-3-methylsulfanyl-butyryl)-2,5-dihydro-1H-pyrrole-2-carbonitrile (20)

(49 mg) LC-MS(ES), m/z: 240 (M+1).

(S,S) 1-(2-Amino-3-cyclohexyl-propionyl)-2,5-dihydro-1H-pyrrole-2-carbonitrile (21)

(30 mg) LC-MS(ES), m/z: 248 (M+1).

1-[2-Amino-3-(1-benzyl-1H-imidazol-4-yl)-propionyl]-2,5-dihydro-1H-pyrrole-2-carbonitrile (22).

(6 mg) LC-MS(ES), m/z: 322 (M+1).

(S,S) 1-(2-Amino-3-mercapto-3-methyl-butyryl)-2,5-dihydro-1H-pyrrole-2-carbonitrile (23)

(23 mg) LC-MS(ES), m/z: 490 (M+Na$^+$). 1H-NMR (MEOH, 200 MHz) δ: 7.24 (m, 15H); 6.23 (m, 1H); 5.98 (m, 1H); 5.57 (m, 1H); 4.60 (m, 2H); 4.30 (s, 1H); 1.58 (s, 3H); 1.52 (s, 3H).

1-[2-Amino-3-(4-methoxy-benzylsulfanyl)-3-methyl-butyryl]-2,5-dihydro-1H-pyrrole-2-carbonitrile (25)

(3 mg) LC-MS(ES), m/z: 346 (M+1).

(S,S) 1-[2-Amino-3-methyl-3-(4-methyl-benzylsulfanyl)]-butyryl-2,5-dihydro-1H-pyrrole-2-carbonitrile (26)

(58 mg) LC-MS(ES), m/z: 330 (M+1). 1H-NMR (MEOH, 200 MHz) δ: 7.32 (d, 2H); 7.13 (d, 2H); 6.20 (m, 1H); 5.95 (m, 1H); 5.52 (m, 1H); 4.42 (m, 2H); 4.07 (s, 1H); 3.90 (dd, 2H); 2.30 (s, 3H); 1.58 (s, 3H); 1.46 (s, 3H).

1-[2-Amino-2-(4-fluoro-phenyl)-acetyl]-2,5-dihydro-1H-pyrrole-2-carbonitrile (27)

(56 mg) LC-MS(ES), m/z: 246 (M+1). 1H-NMR (MEOH, 200 MHz) δ: 7.50 (m, 2H); 7.29 (m, 2H); 6.12 (m, 1H); 5.92, (m, 1H); 5.58 (m, 1H); 5.40 (s, 1H); 4.50 (dd, 1H); 3.75 (m, 1H).

(S,S) 1-(2-Amino-2-indan-4-yl-acetyl)-2,5-dihydro-1H-pyrrole-2-carbonitrile (28)

(65 mg) LC-MS(ES), m/z: 268 (M+1). 1H-NMR (MEOH, 200 MHz) δ: 7.20 (m, 3H); 6.23 (m, 1H); 5.97 (m, 1H); 5.56 (m, 1H); 4.53 (m, 2H); 4.48 (s, 1H); 3.20–2.96 (m, 6H).

(S,S) 1-(2-Amino-3-methyl-butyryl)-2,5-dihydro-1H-pyrrole-2-carbonitrile (29)

(42 mg) LC-MS(ES), m/z: 195 (M+1). 1H-NMR (MEOH, 200 MHz) δ: 6.05 (m, 1H); 5.89 (m, 1H); 5.21 (m, 1H); 4.52–4.38 (m, 2H); 4.15–4.00 (m, 1H); 2.50–2.15 (m, 1H); 1.18 d, 3H); 1.08 (d, 3H).

1-(5,5-Dimethyl-thiazolidine-4-carbonyl)-2,5-dihydro-1H-pyrrole-2-carbonitrile (30)

(115 mg) LC-MS(ES), m/z: 238 (M+1), 1-(1-Amino-cyclopropanecarbonyl)-2,5-dihydro-1H-pyrrole-2-carbonitrile (31)

(45 mg) LC-MS(ES), m/z: 178 (M+1)

(S,S) 1-(2-Amino-3-phenyl-propionyl)-2,5-dihydro-1H-pyrrole-2-carbonitrile (32)

(57 mg) LC-MS(ES), m/z: 242 (M+1). 1H-NMR (MEOH, 200 MHz) δ: 7.34 (s, 5H); 5.95 (m, 1H); 5.83 (m, 1H); 5.45 (m, 1H); 4.45 (m, 1H); 4.25 (m, 1H); 3.33–3.00 (m, 3H)

1-(2-Amino-butyryl)-2,5-dihydro-1H-pyrrole-2-carbonitrile (33)

(60 mg) LC-MS(ES), m/z: 180 (M+1). 1H-NMR (MEOH, 200 MHz) δ: 6.25 (m, 1H); 5.96 (m, 1H); 5.55 (m, 1H); 4.50 (m, 2H); 4.22 (t, 1H); 2.00 (m, 2H); 1.18 (t, 3H).

1-[2-Amino-3-(1H-indol-3-yl)-propionyl]-2,5-dihydro-1H-pyrrole-2-carbonitrile (34)

(53 mg) LC-MS(ES), m/z: 281 (M+1). 1H-NMR (MEOH, 200 MHz) δ: 7.70–7.03 (m, 5H); 5.90 (m, 1H); 5.80 (m, 1H); 5.45 (m, 1H); 4.42 (m, 1H); 4.20 (m, 1H); 3.45–3.15 (m, 3H).

(S,S) 1-(Piperidine-2-carbonyl)-2,5-dihydro-1H-pyrrole-2-carbonitrile (35)

(177 mg) 1H-NMR (MEOH, 300 MHz) δ: 6.25 (m, 1H); 5.98 (m, 1H); 5.53 (m, 1H); 4.49 (m, 2H); 4.15 (m, 1H); 3.43 (m, 1H); 3.08 (m, 1H); 2.29 (m, 1H); 1.95 (m, 2H); 1.71 (m, 3H).

(S,S) 1-(1,2,3,4-Tetrahydro-isoquinoline-3-carbonyl)-2,5-dihydro-1H-pyrrole-2-carbonitrile (36)

(357 mg). 1H-NMR (MEOH, 300 MHz) δ: 7.30 (m, 4H); 6.28 (m, 1H); 6.01 (m, 1H); 5.60 (m, 1H); 4.63–4.42 (m, 5H); 3.52 (dd, 1H); 3.19 (dd, 1H).

1-(2-Amino-cyclopentanecarbonyl)-2,5-dihydro-1H-pyrrole-2-S-carbonitrile (37)

LC-MS(ES), m/z: 206 (M+1).

1-(Piperidine-3-carbonyl)-2,5-dihydro-1H-pyrrole-2-S-carbonitrile (38)

LC-MS(ES), m/z: 206 (M+1).

1-((3R)-Amino-5-phenyl-pentanoyl)-2,5-dihydro-1H-pyrrole-(2S)-carbonitrile (39)

LC-MS(ES), m/z: 270 (M+1).

1-((3S)-Amino-4-phenyl-butyryl)-2,5-dihydro-1H-pyrrole-(2S)-carbonitrile (40)

LC-MS(ES), m/z: 256 (M+1).

1-(Morpholine-2-carbonyl)-2,5-dihydro-1H-pyrrole-2-S-carbonitrile (41)

LC-MS(ES), m/z: 208 (M+1).

1-(3-Amino-6-phenyl-hex-5-enoyl)-2,5-dihydro-1H-pyrrole-2-S-carbonitrile (42)

LC-MS(ES), m/z: 281 (M+1).

1-[(3S)-Amino-4-(4-benzyloxy-phenyl)-butyryl]-2,5-dihydro-1H-pyrrole-(2S)-carbonitrile (43)

LC-MS(ES), m/z: 361 (M+1).

1-(2-Pyrrolidin-2-yl-acetyl)-2,5-dihydro-1H-pyrrole-2-S-carbonitrile (44)

LC-MS(ES), m/z: 206 (M+1).

1-[4-(2-Chloro-phenyl)-pyrrolidine-3-carbonyl]-2,5-dihydro-1H-pyrrole-2-S-carbonitrile (45)

LC-MS(ES), m/z: 302 (M+1).

1-(4-Phenyl-pyrrolidine-3-carbonyl)-2,5-dihydro-1H-pyrrole-2-S-carbonitrile (46)

LC-MS(ES), m/z: 268 (M+1).

Example 2

1-[2-(R,S)-(4-Cyanophenyl)thiazolidine-4-(R)-carbonyl]-2,5-dihydro-1H-pyrrole-2-(S)-carbonitrile (47)

4-Cyanobenzaldehyde (500 mg, 3.8 mmol) was dissolved in 5 ml of ethanol (96%) and L-(+)-cysteine hydrochloride (460 mg, 3.8 mmol) and natriumacetate trihydrate (468 mg, 5.7 mmol) dissolved in 5 ml of water was added. The reaction mixture was stirred for 16 hours at room temperature and the white crystals were collected by filtration and washed twice with 15 ml of water:ethanol (1:1), to afford 400 mg of 2-(RS)-(4-cyanophenyl)thiazolidine-4-(R)-carboxylic acid (48) in 44% yield. 1H-NMR (MEOH, 300 MHz) δ: 7.69 (m, 4H); 5.81 (s, ½H); 5.60 (s, ½H); 4.23 (dd, ½H); 4.02 (dd, ½H); 3.52–3.17 (m, 2H).

(265 mg, 1.13 mmol) of (48) was dissolved in 10 ml of tetrahydrofuran, 5 ml of water, and (0.452 ml, 1.13 mmol) of a 10% aqueous solution of sodium hydroxide. Di-tert.-butyl dicarbonate (321 mg, 1.47 mmol) was added and the reaction mixture was stirred for 5 days. Tetrahydrofuran was evaporated off and the remaining was dissolved in 50 ml of ethyl acetate and 50 ml of water, and solid potassium hydrogen sulphate was added until pH=2. The organic material was extracted into 4×50 ml of ethyl acetate and the combined organic extracts were washed with 100 ml of water, and 100 ml of brine, and dried over sodium sulphate. The solvent was evaporated to afford 340 mg of 2-(RS)-(4-cyanophenyl)thiazolidine-4-(R)-carboxylic acid 3-carboxylic acid tert-butyl ester (49) as beige crystals in 90% yield. 1H-NMR (CDCl3, 300 MHz) δ: 7.62 (m, 4H); 6.21–5.41 (m, 1H); 5.02–4.78 (m, 1H); 3.47–3.21 (m, 2H); 1.42 (s, 3H); 1.24 (s, 6H). LC-MS(ES), m/z: 235.1 (M-99 (BOC) and 357.2 (M+23(Na)).

(49) was coupled to (S) 2,5-dihydro-1H-pyrrole-2-carboxylic acid amide and dehydrated with phosphorus oxychloride and finally deprotected with trifluoroacetic acid as described in example 1, and purified by preparative HPLC to afford 52 mg of the title compound (47). 1H-NMR (MEOH, 300 MHz) δ: 7.75–7.63 (m, 4H); 6.24 (m, 1H); 5.95 (m, 1H); 5.82 (s, ½H); 5.65 (s, ½H); 5.48 (m, 1H); 4.69 (m, 1H); 4.49 (m, 1H); 4.27 (m, 1H) 3.48 (m, 1H); 3.22 (m, 1H). LC-MS(ES), m/z: 311.2 (M+1)

The following compounds were prepared by the route outlined in example 2; however, all compounds were also purified by preparative HPLC after the dehydration step.

1-[2-(R,S)-(1-(R,S)-Phenylethyl)thiazolidine-4-(R)-carbonyl]-2,5-dihydro-1H-pyrrole-2-(S)-carbonitrile (50)

(32 mg) 1H-NMR (MEOH, 300 MHz) δ:) δ: 7.41–7.15 (m, 5H); 6.80 (dd, ½H); 6.45 (dd, ½H); 6.20 (m, 1H); 5.92 (m, 1H); 5.70 (d, ½H); 5.51 (d, ½H); 5.45 (m, 1H); 4.68–4.29 (m, 2H); 4.12–3.88 (m, 1H); 3.81–2.82 (m, 3H); 1.40 (m, 3H). LC-MS(ES), m/z: 314.2 (M+1).

1-(2-(R,S)-Phenylthiazolidine-4-(R)-carbonyl)-2,5-dihydro-1H-pyrrole-2-(S)-carbonitrile (51)

(40 mg) 1H-NMR (MEOH, 300 MHz) δ:) δ: 7.40 (m, 5H); 6.73 (m, ½H); 6.48 (m, ½H); 6.25 (m, 1H); 5.98 (m, 1H); 5.52 (m, 1H); 5.11 (m, 1H); 4.72–3.91 (m, 3H); 3.69–2.91 (m, 2H). LC-MS(ES), m/z: 286.2 (M+1).

1-(Thiazolidine-4-(R)-carbonyl)-2,5-dihydro-1H-pyrrole-2-(S)-carbonitrile (52)

(R)-(−)-Thiazolidine-4-carboxylic acid was used as the starting material instead of L-(+)-cysteine hydrochloride as in example 2. The title compound was synthesised as outlined in example 2, starting at the BOC-protection step, to afford 46 mg of (X+7). LC-MS(ES), m/z: 210 (M+1).

What is claimed is:

1. A compound of formula IV

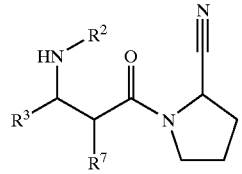

Formula IV wherein
at least one of the bonds in the five-membered ring is a double bond;
$R^2$ is H; $C_1$–$C_{10}$ alkyl optionally substituted with one or more $R^4$ independently; $C_2$–$C_{10}$ alkenyl optionally substituted with one or more $R^4$ independently;

$C_2$–$C_{10}$-alkynyl optionally substituted with one or more $R^4$ independently; $C_3$–$C_{10}$-cycloalkyl optionally substituted with one or more $R^4$ independently; $C_5$–$C_{10}$ cycloalkenyl optionally substituted with one or more $R^4$ independently; aryl optionally substituted with one or more $R^5$ independently;

$R^3$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$-alkynyl optionally substituted with one or more $R^4$ independently; $C_3$–$C_{10}$ cycloalkyl optionally substituted with one or more $R^4$ independently; $C_5$–$C_{10}$ cycloalkenyl optionally substituted with one or more $R^4$ independently; aryl optionally substituted with one or more $R^5$ independently and optionally fused to a $C_3$–$C_{10}$ cycloalkane;

$R^2$ is optionally connected to $R^3$ or $R^7$ by a saturated or unsaturated bridge containing 1–3 carbon atoms, nitrogen atoms, thus forming a ring, said ring is optionally fused to an aryl optionally substituted by one or more $R^5$ independently;

$R^4$ is cycloalkyl; aryl optionally substituted with one or more $R^5$ independently;

$R^5$ is halogen, $C_1$–$C_{10}$ alkyl, $C_1$–$C_{10}$ alkoxy, benzyl;

$R^6$ is $C_1$–$C_{10}$ alkyl, $C_2$–$C_{10}$ alkenyl, $C_2$–$C_{10}$-alkynyl, $C_3$–$C_{10}$-cycloalkyl, $C_5$–$C_{10}$ cycloalkenyl where any one of said alkyl, alkenyl, alkynyl, cycloalkyl, or cykloalkenyl is optionally substituted with aryl optionally substituted with one or more $R^5$ independently or heteroaryl optionally substituted with one or more $R^5$ independently; benzyl, phenethyl; aryl optionally substituted with one or more $R^5$ independently; or heteroaryl optionally substituted with one or more $R^5$ independently;

$R^7$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$-alkynyl optionally substituted with one or more $R^4$ independently; $C_3$–$C_{10}$-cycloalkyl optionally substituted with one or more $R^4$ independently; $C_5$–$C_{10}$ cycloalkenyl optionally substituted with one or more $R^4$ independently; aryl optionally substituted with one or more $R^5$ independently, halogen, $C_1$–$C_{10}$ alkoxy, $C_1$–$C_{10}$ alkylthio, $C_1$–$C_{10}$ alkylamino, $C_1$–$C_{10}$ dialkylamino, hydroxymethyl, nitro, trifluoromethyl, trifluoromethoxy, trifluoromethylthio, N-hydroxyimino, cyano; carboxy; acetamido; hydroxy; sulfamoyl, carbamoyl;

with the proviso that the groups $R^2$, $R^3$, and $R^7$ cannot all be H or a salt thereof with a pharmaceutically acceptable acid or base.

2. A compound of claim 1, wherein
$R^2$ is H; $C_1$–$C_{10}$ alkyl optionally substituted with $R^4$; $C_2$–$C_{10}$ alkenyl optionally substituted with $R^4$; $C_2$–$C_{10}$-alkynyl optionally substituted with $R^4$; aryl optionally substituted with one or more $R^5$ independently; or $R^2$ is connected to $R^3$ or $R^7$ by a saturated or unsaturated bridge containing 1–3 carbon atoms, nitrogen atoms, thus forming a ring, said ring is optionally fused to an aryl optionally substituted by one or more $R^5$ independently.

3. A compound of claim 2, wherein $R^2$ is H or $C_1$–$C_{10}$ alkyl optionally substituted with $R^4$.

4. A compound of claim 3, wherein is H.

5. A compound of claim 1, wherein $R^3$ is H; $C_1$–$C_{10}$ alkyl optionally substituted with $R^4$; $C_2$–$C_{10}$ alkenyl optionally substituted with $R^4$; $C_2$–$C_{10}$-alkynyl optionally substituted with $R^4$; $C_3$–$C_{10}$ cycloalkyl optionally substituted with $R^4$; aryl optionally substituted with one or more $R^5$ independently and is optionally fused to a $C_3$–$C_{10}$ cycloalkane.

6. A compound of claim 5, wherein $R^3$ is H $C_1$–$C_{10}$ alkyl optionally substituted with $R^4$; or aryl optionally substituted with one or more $R^5$ independently and is optionally fused to a $C_3$–$C_{10}$ cycloalkane.

7. A compound of claim 6, wherein $R^3$ is $C_1$–$C_{10}$ alkyl optionally substituted with $R^4$.

8. A compound of claim 1, wherein $R^4$ is aryl optionally substituted with one or more $R^5$ independently.

9. A compound of claim 1, wherein $R^5$ is halogen, $C_1$–$C_{10}$ alkyl, or $C_{1-10}$ alkoxy.

10. A compound of claim 1, wherein $R^6$ is $C_1$–$C_{10}$ alkyl, $C_2$–$C_{10}$ alkenyl optionally substituted with $R^4$; $C_2$–$C_{10}$-alkynyl optionally substituted with $R^4$; benzyl, aryl optionally substituted with one or more $R^5$ independently, or heteroaryl optionally substituted with one or more $R^5$ independently.

11. A compound of claim 10, wherein $R^6$ is $C_1$–$C_{10}$ alkyl, benzyl, or aryl optionally substituted with one or more $R^5$ independently.

12. A pharmaceutical composition comprising as a active ingredient at least one compound of claim 1 or a pharmaceutically acceptable salt or prodrug or hydrate thereof together with a pharmaceutically acceptable carrier or diluent.

* * * * *